Figure 1:
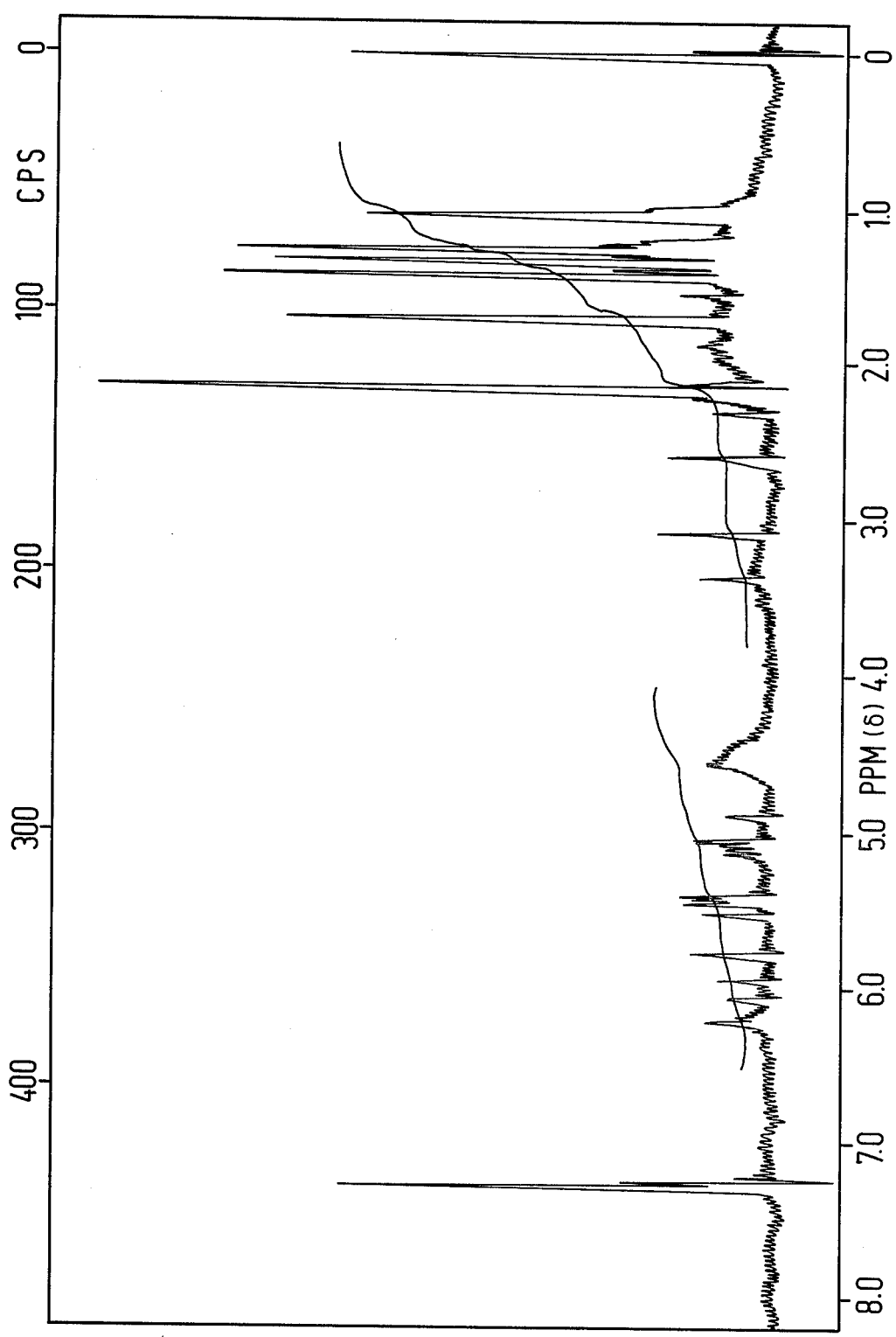

United States Patent [19]

Bhat et al.

[11] 4,088,659

[45] May 9, 1978

[54] EFFECTIVE SUBSTANCE FROM PLANTS BELONGING TO THE LABIATAE FAMILY

[75] Inventors: Sujata Vasudev Bhat, Thana, East; Noèl John de Souza, Bombay; Horst Dornauer, Bombay; Bani Kanta Bhattacharya, Bombay; Alihusein Nomanbhai Dohadwalla, Bombay, all of India

[73] Assignee: Hoechst Aktiengesellschaft, Frankfurt am Main, Germany

[21] Appl. No.: 751,967

[22] Filed: Dec. 17, 1976

[30] Foreign Application Priority Data

Dec. 22, 1975 Germany .............................. 2557784

[51] Int. Cl.$^2$ .................. C07D 311/02; A61K 35/78; A61K 31/35
[52] U.S. Cl. ................................ 260/345.2; 424/195; 424/283
[58] Field of Search ...................... 424/195; 260/345.2

[56] References Cited

U.S. PATENT DOCUMENTS

| | | | |
|---|---|---|---|
| 3,816,458 | 6/1974 | Saucy | 260/345.2 |
| 3,901,924 | 8/1975 | Auger et al. | 260/345.2 |

OTHER PUBLICATIONS

Chemical Abstracts vol. 76:83347m (1972); vol. 77:140336d (1972); vol. 79:78982x (1973) & vol. 83:p.882 (1975).

J. Am. Chem. Soc./95:2/ Jan. 24, 1973, pp. 598–600 & /96:2/ Jan. 23, 1974, pp. 580–581.

*Primary Examiner*—Donald B. Moyer
*Attorney, Agent, or Firm*—Curtis, Morris & Safford

[57] ABSTRACT

Extraction processes are described resulting in the isolation of a pharmacologically active substance from a plant of the Labiatae family. Chemical and physical properties of this compound are given in the specification. Because of its vasodilating and blood pressure lowering effect the compound is useful as a drug for the treatment of hypertension.

1 Claim, 2 Drawing Figures

EFFECTIVE SUBSTANCE FROM PLANTS BELONGING TO THE LABIATAE FAMILY

The present invention relates to a pharmacologically effective substance isolated from plants belonging to the Labiatae family, to a process for the isolation of that substance from the plant material and to therapeutical preparations containing it as active substance.

The Labiatae family comprises about 3500 plant species distributed over about 180 genera. Among these 180 genera are the plants classified as Plectranthus, Coleus, Anisochilus, Lavandula and Leonitis. About thirty Plectranthus species are found to grow in India, of which *P. macranthus, P. mollis, P. stocksii, P. coetsa,* and *P. incanus* are the more common plants. There are about nine Coleus species to be found in India bearing the names *C. amboinicus, C. forskohlii, C. malabaricus, C. parviflorus, C. spicatus, C. rotundifolius, C. scutellarioides, C. blumei* and *C. lacinatus.* In the Anisochilus group, the species *A. carnosus* and *A. verticillatus* are the two more commonly growing plants of the thirteen reported to be found in India. The plants of interest in the Lavandula genera are *L. bipinatta, L. officinalis, L. gibsoni* and *L. burmanni. Leonotis nepetaefolia* is the more common plant of the two Leonitis species found to grow in India.

The present invention relates to a process for the isolation of a pharmacologically effective substance from the aforementioned plants belonging to the Labiatae family. A process for the isolation of a pharmacologically effective substance from *Coleus forskohlii* belonging to the Labiatae family is preferred.

*Coleus forskohlii* is an Indian herb belonging to the Labiatae family and is synonymous with *Coleus barbatus* (Benth.). The plants grow in different parts of India and are commonly to be found in the subtropical Himalayan region, the Deccan Peninsula, Gujarat, Bihar and South India. The plants are also cultivated in several places in India, namely Bombay, Gujarat and Saurashtra. The morphological details and distribution of *Coleus forskohlii* are fully described (cf. The Wealth of India, Vol. 11, C.S.I.R., India, 1950, page 308).

A pharmacologically effective substance has been obtained from a plant of the Labiatae family which substance has principally a blood pressure lowering property and a positive inotropic effect. Preferably the roots of *Coleus forskohlii* are used for isolation of the pharmacologically effective substance.

The present invention provides a process for the isolation of a pharmacologically effective substance from a plant of the Labiatae family which comprises extracting the dried and ground plant material with a hydrocarbon and then with solvents like aromatic hydrocarbons, aromatic and aliphatic halogenated hydrocarbons, dialkyl ethers, dialkyl ketones, alkanols, carboxylic acids and their esters or any solvent which will dissolve the desired pharmacologically effective substance, such solvents being for example dimethyl formamide and dimethyl sulfoxide, evaporating the extract to give a residue, either treating the residue with an alkanol and filtering the suspension to provide an alkanolic solution, or partitioning the residue between a pair of immiscible solvents, only one of which is capable of dissolving the desired pharmacologically effective substance, evaporating the alkanolic solution or the solution containing the desired substance to give a residue, subjecting the residue to column chromatography, evaporating the chromatographic fractions containing the desired substance to give a residue and recrystallizing the residue.

Two operational methods are preferred. In the first one, a plant of the Labiatae family is extracted with a hydrocarbon having 5 to 10 carbon atoms and then with a halogenated hydrocarbon having 1 to 3 carbon atoms and up to 6 halogen atoms, the halogenated hydrocarbon extract is evaporated to give a residue, the residue is extracted with an alkanol having 1 to 6 carbon atoms, the alkanol extract is evaporated to give a residue, and the resulting residue is subjected to column chromatography, the eluted fractions containing the product are evaporated to give a residue and the residue is crystalized to give the pharmacologically active substance.

More particularly, the invented process comprises extracting dried roots of the plant *Coleus forskohlii* with an aliphatic halogenated hydrocarbon having 1 to 3 carbon atoms and up to 6 halogen atoms, preferably chlorine atoms, evaporating the extract to give a residue, treating the residue with a lower alkanol having 1 to 6 carbon atoms, removing the insoluble residue by filtration, evaporating the alkanolic filtrate to give a residue, subjecting the residue to column chromatography, preferably on silica gel or alumina using as eluants the usual organic solvents of increasing polarity known to those skilled in the art, evaporating the fractions containing the desired product and recrystallizing the resulting residue.

In the second operational method, a plant of the Labiatae family is extracted with a hydrocarbon having 5 to 10 carbon atoms and then with an alkanol having 1 to 6 carbon atoms, the alkanolic extract is evaporated to give a residue, the residue is partitioned between a pair of immiscible solvents, one of which must be capable of dissolving the pharmacologically effective substance, the solution is evaporated to give a residue and the residue so obtained is subjected to column chromatography, the eluted fractions containing the product are evaporated to give a residue and the residue is recrystalized to give the pharmacologically active substance according to the invention.

More particularly, the second invented process comprises extracting the dried roots of the plant *Coleus forskohlii* with an aliphatic alkanol having 1 to 6 carbon atoms, preferably methanol or ethanol, evaporating the extract to give a residue, partitioning the residue between two immiscible solvents, one of which is capable of dissolving the desired substance, preferably chloroform/water or benzene/water, evaporating the organic solvent layer to give a residue, subjecting the residue to column chromatography, preferably on silica gel or alumina, using as eluants the usual organic solvents of increasing polarity known to those skilled in the art, evaporating the fractions containing the desired product and recrystallizing the residue.

It is advantageous in both operational methods to use the preferably dried and ground roots of *Coleus forskohlii* and to subject these to a previous extraction with a hydrocarbon solvent in order to eliminate the main part of the plant fats and waxes present. There are advantageously used hydrocarbons having 5 to 10 carbon atoms, preferably petroleum ether, pentane or hexane in the ratio of 1 : 2 to 1 : 10 parts by weight of plant material to solvent.

For extracting the active substance from *Coleus forskohlii,* aliphatic halogenated hydrocarbons having 1 to 3 carbon atoms and up to 6 halogen atoms, preferably up to 6 chlorine atoms or alkanols having 1 to 6 carbon atoms are used. From these solvents chlorinated alkanes, especially methylene chloride and chloroform or alkanols, especially methanol and ethanol, are preferred. The extracting agents are preferably used in the ratio of 1 : 2 to 1 : 10 parts by weight of plant material to extracting agent.

The halogenated hydrocarbon extract or the alkanol extract is concentrated under reduced pressure, for example, in vacuo, to give a residue. Depending on the extract from which the residues are obtained, the residues are now processed differently as described in the next two consecutive paragraphs and as depicted in the accompanying flow-sheet diagram of the isolation procedure.

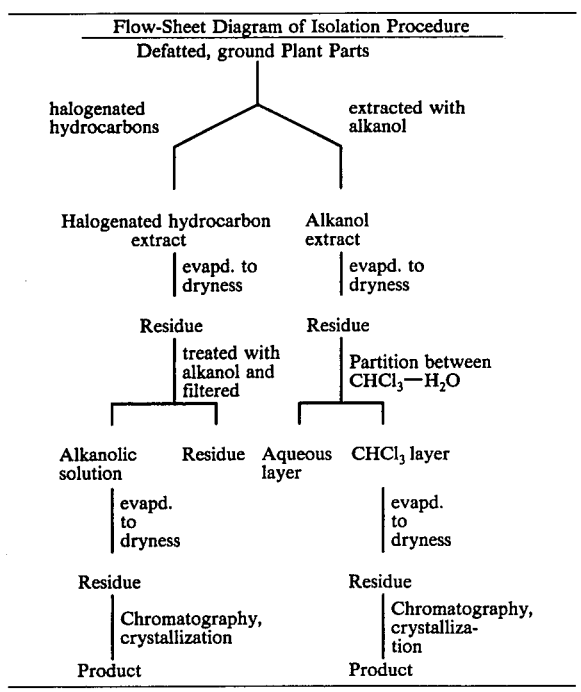

The residue from the halogenated hydrocarbon extract is extracted with a lower alkanol having from 1 - 6 carbon atoms, such as for example methanol which is preferred, until the removal of alkanol soluble material is complete. The volume of alkanol used is preferably in the ratio of 1 : 10 to 1 : 40 parts by weight of residue to alkanol. The alkanolic extracts are combined and filtered to give an alkanolic solution.

The second process for treating the residue from the alkanol extract is partitioning the residue between a pair of immiscible solvents, one of which is capable of dissolving the desired pharmacologically effective substance, and the other is a solvent in which the desired substance is insoluble, such a pair of solvents being preferably chloroform and water. An approximately 1 : 1 (V : V) mixture of chloroform — water is preferably used. The chloroform layer is separated.

The resulting alkanolic solution of the first process or the organic solvent layer of the second process is evaporated to dryness under reduced pressure, preferably in vacuo, and the residue is subjected to chromatography, preferably on a column of silica gel or alumina using as eluants organic solvents or mixtures of these solvents of increasing polarity known to those skilled in the art. The preferred organic solvents used as eluants for column chromatography are: petroleum ether (B.p. 60°-80° C), petroleum ether-benzene mixtures, benzene, benzene-ethyl acetate or benzene-chloroform mixtures, ethyl acetate-methanol or chloroform-methanol mixtures and methanol. The fractions eluted by benzene-ethyl acetate or benzene-chloroform and containing the desired compound as indicated by thin-layer chromatography are combined and evaporated to dryness under reduced pressure, preferably in vacuo, and the residue is recrystallized from organic solvents, preferably ethyl acetate/petroleum ether (b.p. 60°-80° C) to give a colorless crystalline product melting at 230°-232° C which is the pharmacologically active substance of the present invention.

The molecular formula of the active substance is $C_{22}H_{34}O_7$ which has been computed from the molecular weight of 410 mass units determined by mass spectrometry and from the following elemental analytical data: C 64 - 65% and H=8 - 8.5%. $C_{22}H_{34}O_7$ requires C = 64.37 and H = 8.35%.

Figure 2:
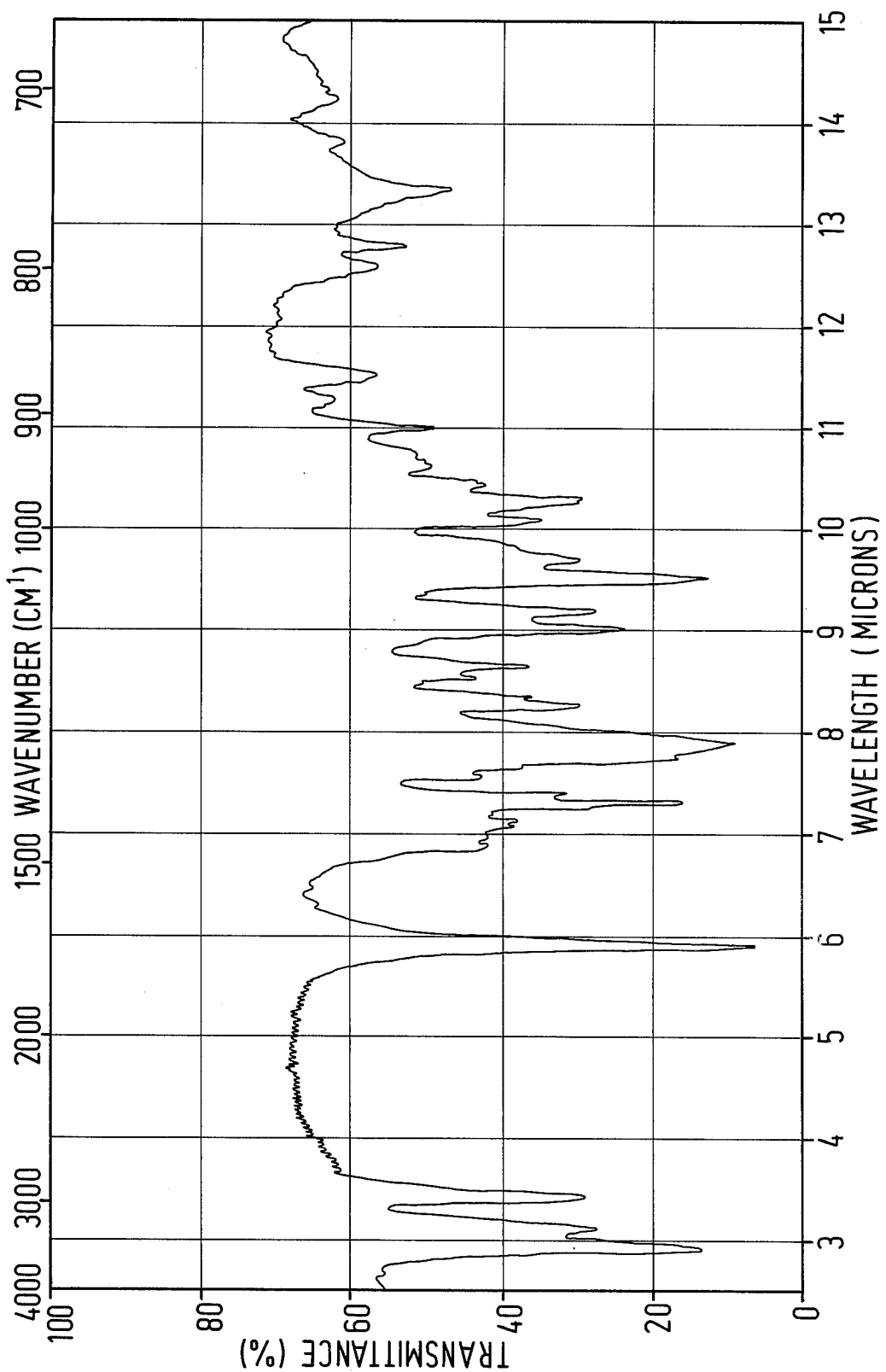

In general the following data are found: The ultraviolet spectrum shows absorption at λ max 208–210 (ε max 900–1200) and 305–310 nm (ε max 45–55), and the specific rotation $[\alpha]_D^{25}$ is −20° to −30° (c= 1.7 in $CHCl_3$). More specifically, the following data are likely to be found:

The ultraviolet spectrum shows absorption at λ max 210 (ε max 1000) and 305 nm (ε max 50), and the specific rotation $[\alpha]_D^{25}$ is −25° to −27° (C = 1.68 in $CHCl_3$). The infrared and nuclear magnetic resonance spectra are shown in FIGS. 1 and 2 of the accompanying drawings.

The active substance is soluble in organic solvents such as methanol, ethanol, propanol, acetone, chloroform, methylene chloride, ethyl acetate, benzene and ether.

The active substance exhibits physical and chemical properties usually shown by terpenoids. Several crystalline derivatives have been made, some of which are for example (a) a dihydro derivative, m.p. 245°-8°, (b) an acetate, m.p. 199°-205°, and (c) a methyl ether, m.p. 174°-176°. The spectral and chemical data reveal that the active substance is a diterpenoid possessing a labd-14-ene carbon skeleton

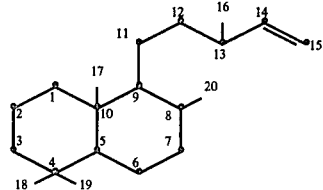

bearing oxygen-containing functional groups and which is substituted in such a way that it also has the following structural features:

(a) two secondary hydroxy groups,
(b) one tertiary hydroxy group,
(c) an oxide group,
(d) one acetoxy group and
(e) one keto group.

The spectral and chemical data reveal, in particular, that the active substance has the structure represented by the formula

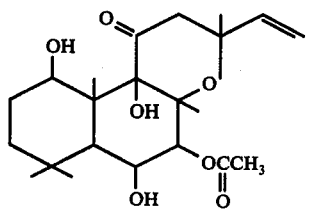

It is to be understood that the formula encompasses all possible stereoisomers of the compound and mixtures thereof.

The new active substance according to the invention is characterized by a very good hypotensive effect. It has peripheral vasodilatation and mild central nervous system depressant activity.

Due to its blood pressure lowering action the active substance of the invention is suitable for the treatment of cardiac and circulatory diseases, for example essential and malignant hypertonia, cardiac insufficiency, Angina pectoris, and disturbances of the peripheral circulation. The active substance can be used for therapeutical purposes in combination with other pharmacologically active substances, for example diuretics, antiarrhythmica, β-blockers, tranquillisers, cardiodilatatory agents, hypolipidemics, etc.

The positive inotropic effect of the substance will be useful as an adjunct therapy to cardioactive glycosides in congestive heart failure, in collapse due to haemorrhage and in surgical shock.

The active substance of the invention can be administered perorally or intravenously. The severity of the disease and the weight of the patient determine the daily dose to be administered, which may vary within 25 mg and 1,000 mg.

For the administration per os. tablets and dragees are considered which contain the active substance in an amount of 25 to 1,000 mg, and the usual auxiliaries and carriers, for example talcum, starch, lactose, etc. For intravenous administration solutions or suspensions of the active substance in a pharmaceutically tolerated vegetable oil, for example peanut oil or sesame oil and alcoholic solutions of the active substance, for example ethanol, propanediol or glycerol or in mixtures of the above solvents are considered.

The following Examples illustrate the extraction of the new active substance from *Coleus forskohlii*. The possibilities of extraction are, however, not limited to these examples.

EXAMPLE 1

Dried and ground roots of *Coleus forskohlii* (12 kg) were extracted twice with 15 l portions of petroleum ether (b.p. 60°-80°). The roots were then repeatedly extracted with 15 l portions of methylene chloride till they were exhaustively extracted. 60 l methylene chloride were used. The combined methylene chloride extracts were filtered and evaporated in vacuo. The residue (ca. 200 g) was extracted twice with 3 l portions of methanol. The combined methanol extracts were filtered and the methanolic filtrate was evaporated in vacuo. The residue (ca. 130 g) was chromatographed on a silica gel column using as eluants the following solvents: petroleum ether (b.p. 60°-80°), petroleum ether-benzene mixtures, benzene, benzene-ethyl acetate mixtures, ethyl acetate, ethyl acetate-methanol mixtures and methanol. The appropriate benzene-ethyl acetate eluted fractions containing the desired compound, as indicated by monitoring the eluted fractions by thin-layer chromatography and/or by testing for pharmacological activity, were combined and evaporated to dryness in vacuo. The residue was recrystallized from ethyl acetate-petroleum ether (b.p. 60°-80°) to give colorless crystals in a yield of 8.6 g, which crystals had the properties indicated earlier herein.

EXAMPLE 2

Dried and ground roots of *Coleus forskohlii* (12 kg) were extracted twice with 15 l portions of petroleum ether (b.p. 60°-80°). The roots were then repeatedly extracted with 25 l of methanol, till they were exhaustively extracted. 100 l of methanol were used. The combined methanol extracts were filtered and evaporated in vacuo. The residue (ca. 650 g) was partitioned between 2 l portions of chloroform and 2 l portions of water each, and the chloroform layer was separated. The aqueous layer was repeatedly extracted with 2 l portions of chloroform. The combined chloroform extracts were filtered, dried over sodium sulfate and evaporated in vacuo. The residue (about 300 g) was chromatographed on a silica gel or alumina column and worked up as in Example 1. Colorless crystals (9.0 g) were obtained which had the properties indicated earlier.

EXAMPLE 3

15 kg of dried and ground whole plants of *Coleus forskohlii* were treated according to the process described in Examples 1 and 2 and yielded 8.5 g of active substance; this active substance had the properties indicated earlier.

EXAMPLE 4

12 kg of dried and ground roots of *Coleus forskohlii* were extracted as described in the first paragraph of Example 1. The residue (ca. 130 g) was chromatographed on an alumina column using as eluants the following solvents: petroleum ether (b.p. 60°-80°), petroleum ether-benzene mixtures, benzene, benzene-chloroform mixtures, chloroform, chloroform-methanol mixtures and methanol. The appropriate benzene-chloroform eluted fractions after evaporation to dryness in vacuo and recrystallization of the residue from ethyl acetate-petroleum ether (b.p. 60°-80° C) gave 8.1 g of active substance which substance had the properties indicated earlier herein.

What is claimed is:

1. A compound, in purified and isolated form, of the formula

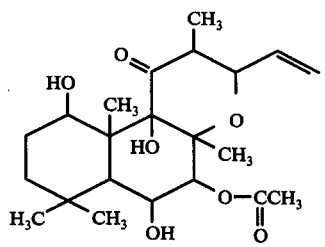

* * * * *

UNITED STATES PATENT AND TRADEMARK OFFICE
CERTIFICATE OF CORRECTION

PATENT NO. : 4,088,659
DATED : May 9, 1978
INVENTOR(S) : Bhat et al.

It is certified that error appears in the above-identified patent and that said Letters Patent are hereby corrected as shown below:

In claim 1, the structural formula should be corrected to read:

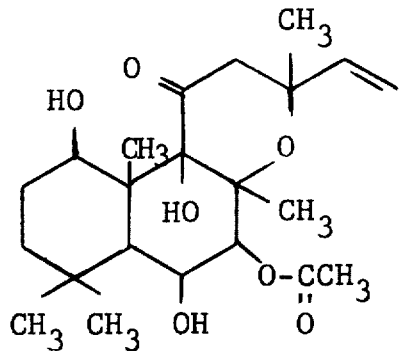

[SEAL]

Signed and Sealed this

Seventeenth Day of October 1978

*Attest:*

RUTH C. MASON
*Attesting Officer*

DONALD W. BANNER
*Commissioner of Patents and Trademarks*